(12) United States Patent
Brottier

(10) Patent No.: US 8,764,738 B2
(45) Date of Patent: *Jul. 1, 2014

(54) SKIN TREATMENT DEVICE USING PULSED ELECTROMAGNETIC RADIATION

(71) Applicant: Vincent Yves Brottier, Adainville (FR)

(72) Inventor: Vincent Yves Brottier, Adainville (FR)

(73) Assignee: Vincent Yves Brottier, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/658,095

(22) Filed: Oct. 23, 2012

(65) Prior Publication Data

US 2013/0123762 A1    May 16, 2013

Related U.S. Application Data

(63) Continuation of application No. 12/388,348, filed on Feb. 18, 2009, now Pat. No. 8,469,949.

(30) Foreign Application Priority Data

Feb. 22, 2008 (FR) ...................................... 08 51770

(51) Int. Cl.
  *A61B 18/18* (2006.01)
  *A61B 18/00* (2006.01)

(52) U.S. Cl.
  CPC ....... *A61B 18/18* (2013.01); *A61B 2018/00452* (2013.01); *A61B 2018/00476* (2013.01)
  USPC .......................................................... 606/9

(58) Field of Classification Search
  CPC ........... A61B 2018/00452; A61B 2018/00476; A61B 18/203; A61B 18/20; A61B 18/18
  See application file for complete search history.

(56) References Cited

U.S. PATENT DOCUMENTS

| 6,162,218 | A  | * | 12/2000 | Elbrecht et al. | 606/41 |
| 6,530,918 | B1 | * | 3/2003  | Ueno et al.     | 606/10 |
| 2003/0004501 | A1 | * | 1/2003 | Wilkens et al.  | 606/9  |
| 2007/0239143 | A1 | * | 10/2007 | Altshuler et al. | 606/9 |
| 2007/0255265 | A1 | * | 11/2007 | Davenport et al. | 606/9 |

* cited by examiner

*Primary Examiner* — Gary Jackson
*Assistant Examiner* — Scott T. Luan
(74) *Attorney, Agent, or Firm* — Miller, Matthias & Hull LLP

(57) ABSTRACT

The device includes a housing, a flash lamp arranged inside the housing, the housing having an opening through which electromagnetic energy originating from the flash lamp can be transmitted towards a skin surface. The housing includes a cavity adjacent to the flash lamp; at least one aeration orifice; and at least one mobile component in the housing, which can be displaced between a first so-called aeration position, in which the cavity communicates with the aeration orifice and a second so-called closed position, for which the cavity is closed in order to limit the light escaping from the opening. The mobile component can be formed by a housing portion that can close the cavity except for the opening, by moving towards a complementary housing portion

13 Claims, 4 Drawing Sheets

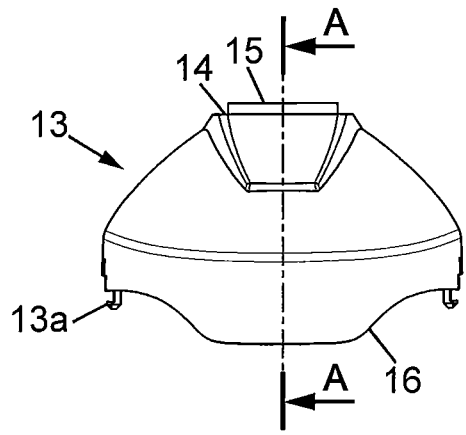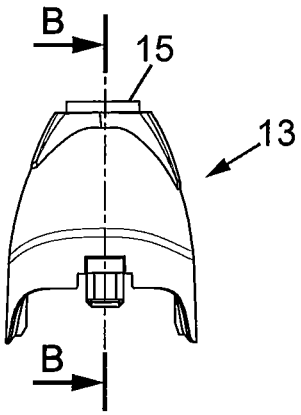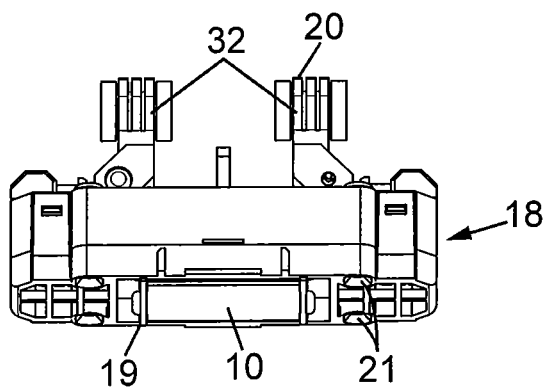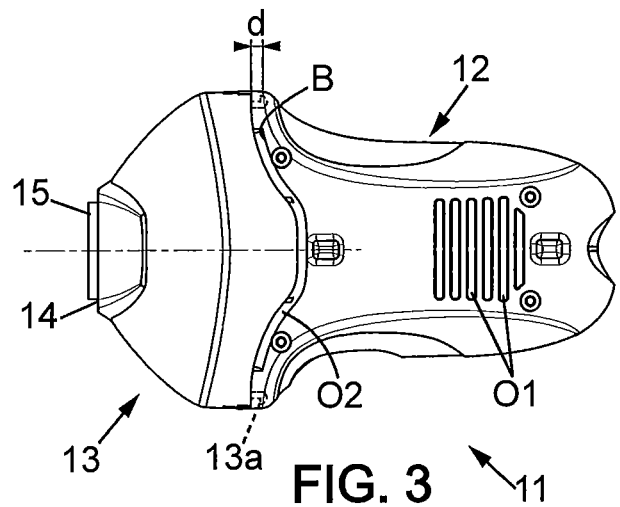

SKIN TREATMENT DEVICE USING PULSED ELECTROMAGNETIC RADIATION

CROSS-REFERENCE TO RELATED APPLICATIONS

This application is a 35 USC §120 continuation of U.S. Ser. No. 12/388,348 filed on Feb. 18, 2009, which claims priority under the Paris Convention to French Patent Application No. 08 51170, filed on Feb. 22, 2008.

FIELD OF THE DISCLOSURE

The present invention relates to the appliances used for local cutaneous applications and emitting visible and/or infrared (V/IR) radiation pulses, these pulses being generated by an incoherent electromagnetic energy source such as a flashlamp—generally xenon—in which electric energy previously stored in one or more capacitors is discharged.

More particularly, the invention relates to a skin treatment device intended for hair removal, comprising a housing, a flashlamp, a coupler, a filter inserted between the flashlamp and the coupler, a first fixing arrangement for fixing the filter in the housing, a second fixing arrangement for fixing the flashlamp in the housing, the coupler making it possible to direct electromagnetic energy originating from the flashlamp onto a skin surface.

BACKGROUND OF THE DISCLOSURE

These appliances produce pulses the duration of which is generally comprised between 5 and 80 ms, which is exceptionally long for a flash and, for this raison, presents specific heat dissipation problems.

In this type of appliance, the high-power flashlamps (dedicated to phototherapy) for dispensing an intense pulsed light have a water cooling system. Typically, the xenon tube is immersed in a closed cavity in which the cooling liquid circulates. This liquid is circulated by a pump. It passes into a radiator in order to allow heat diffusion. The radiator is associated with a large, powerful fan.

One of the drawbacks of the water cooling systems is the requirement to guarantee a perfectly watertight circuit, in particular at the lamp. This systematically results in an increase in the bulk and weight of the appliance. Moreover, pollution of the cooling liquid regularly occurs, which leads to pollution of the lamp (walls). Premature ageing of the lamp makes it necessary to change the lamp, resulting in more frequent unavailability of the appliance.

A need therefore exists for compact appliances that do not have the major drawbacks linked to a water cooling circuit.

SUMMARY OF THE PRESENT DISCLOSURE

A purpose of the present invention is therefore to provide a hair-removal device that is equipped with a compact system for effectively diffusing the heat generated by the use of the flashlamp.

To this end, the housing of the hair-removal device comprises:
  a cavity adjacent to the flashlamp;
  at least one aeration orifice; and
  at least one component which is mobile in the housing, and which can be displaced between a first so-called aeration position, in which said cavity communicates with said aeration orifice and a second so-called closed position, for which said cavity is closed in order to limit the light escaping from the opening.

By means of these arrangements, it is possible to produce a flashlamp hair-removal device the heating of which is effectively limited and which saves costs due to the elimination of the pipes, the pump and the radiator, not to mention the different joints. Furthermore the bulk is reduced. A simple local reduced format fan or even diffusion by natural convection can suffice to ventilate the surface of the filter between two flashes.

Furthermore, the applicator that incorporates the lamp can be designed as an autonomous element, with or without a cord connecting it to a base that does not include a cooling circuit for example. This results in a greater ease of handling, allowing a single individual to carry out hair removal on any surface of their own skin. By way of non-limitative example, the housing can have a component which, when the flashlamp is fixed, moves the interface or end coupler of the device closer to the flashlamp or vice versa, for example by a simple pushing movement.

According to another feature, the housing has:
  a first housing portion having the opening; and
  a second housing portion allowing a displacement in translation between the first housing portion and the second housing portion, the flashlamp being integral with the second housing portion, the mobile component being formed by one of the first and second portions.

Thus, the device according to the invention remains simple in design with one portion that is mobile in relation to the other which is held fixed when the housing is closed.

According to another feature, the first housing portion is a head and the second housing portion forms a handle that can be grasped by a hand, which makes it possible to move the flashlamp closer to the free end of the head when the head is supported on a surface outside the device. Thus, the housing is easy to handle and actuation can be carried out intuitively just after arranging the head so that it is supported via the coupler on the skin surface to be treated.

According to another feature, the device comprises inside the housing:
  a coupler making it possible to direct the electromagnetic energy originating from the flashlamp onto a skin surface;
  a filter inserted between the flashlamp and the coupler;
  a first fixing arrangement for fixing the filter in the housing; and
  a second fixing arrangement for fixing the flashlamp in the housing;
the mobile component moving at least one of the first and second fixing arrangements, the flashlamp being arranged substantially opposite and at a distance from the filter for said first position, the flashlamp and the filter being moved close together for said closed position.

Thus, the surface of the filter can be cooled down during each intermediate period between two flashes.

According to another feature, the first fixing arrangement possesses a degree of freedom in translation between the coupler and the flashlamp, the first fixing arrangement being held at a distance from the coupler by at least one elastic stress component placed on the periphery of the coupler. Thus, the elastic return force exerted on the first fixing arrangement makes it possible to arrange the filter at a distance from the coupler by default. It will be understood that the actuation of the drive connection or mechanism simultaneously allows the lamp to move closer to the filter on the one hand, and the filter closer to the coupler on the other hand.

According to another feature, the first fixing arrangement comprises a tubular-shaped support that comprises on the side opposite the coupler, elastic clipping tabs holding between them the filter, the housing comprising a tubular portion surrounding the support and making it possible to guide the support. Thus, due to the presence of the support, the filter can be displaced in translation without the risk of being altered mechanically.

According to another feature, the second fixing arrangement forms with the flashlamp an expendable unit that can be removed from the housing and comprises a box for accommodating the flashlamp, said box having:

an end surface having a window to allow the rays from the flashlamp to escape;

first fixing elements defining ends opposite said end surface;

second fixing elements arranged on the periphery of the window;

the first fixing elements being configured to engage with at least one piece elongated in a first direction, whilst the second fixing elements are configured to engage with at least one component elongated in a second direction perpendicular to the first direction.

By means of these arrangements, the expendable unit fits perfectly inside the housing of the hair-removal device, generating minimum bulk, and effectively contributes to the kinematics of moving the flashlamp and the filter closer to each other.

According to another feature, the inside of the housing has a surface for guiding a flow of air parallel to the filter and from which said elongated component extends in a direction generally perpendicular to the filter. The guiding surface makes it possible to guide the flow of air between the filter and the lamp in the active position of the device (for example 2-3 mm).

According to another feature, said elongated component has a shoulder and ends in a rod end portion, the box comprising at least one recess with a base and a spring provided in the recess, the recess making it possible to receive at least part of said elongated component, the spring having a first end supported on the base and a second end supported on the shoulder of the elongated component, said spring being compressed for said closed position in which the flashlamp and the filter are moved close together. By means of these arrangements, the box accommodating the lamp automatically returns to its rest position, retracted in relation to the filter.

According to another feature, the first fixing elements comprise metal power conducting elements for supplying the flashlamp. Thus, the flashlamp can be powered by a generator integrated into the housing, for example in the part forming a handle. This makes it possible to optimize the ergonomics of the components inside the housing. The appliance made up of the housing, the flashlamp, the filter and the coupler forms an autonomous assembly. It will be understood that the presence of an electrically conductive connection in fixing elements involved in the drive system allows the user to change the expendable unit without having to disconnect/connect additional connectors inside the housing.

According to another feature, the second fixing arrangement comprises a box making it possible to accommodate the flashlamp and having metal power conducting elements extending opposite the coupler, the second mobile housing portion having at least one substantially cylindrical metal part to which the power conducting elements are fixed.

Thus, the electric contact to the lamp can be produced via cylinders constituted by a solid mass of a conductive material, for example copper (which makes it possible to optimize the efficiency of the power supply to the flashlamp).

According to another feature, the box has a window that allows a plurality of rays to escape from the flashlamp in a determined general orientation, the first housing portion having at least one elongated part to guide the box along an axis parallel to said determined general orientation. Thus, the movement of the flashlamp is made secure, only a straight translation being permitted.

According to another feature, the device comprises a generator to which the flashlamp is connected, a sensor capable of delivering a piece of information representative of the occupation of said closed position by said mobile component, and a control device associated with the generator, configured to receive at least one piece of information from the sensor and allow the emission of a single flash of light when said closed position has been detected by the sensor. Thus, multiple flashes of light onto the same treatment surface in a short period of time are prevented.

Moreover, a subject of the invention is also an expendable unit for a device according to the invention, characterized in that it comprises:

a flashlamp;

a box for accommodating the flashlamp, having an end surface with a window to allow rays from the flashlamp to escape;

on the side of the end surface and on the periphery of the window, at least one recess in which a spring is placed which has an end mobile between a compressed retracted position allowing the cavity of the device to be closed in order to limit light escaping except towards the opening and an extended position for which the cavity communicates with the aeration orifice of the device; and at least one element for fixing the box to the housing, having a stop surface that is oriented in an opposite direction with respect to the thrust direction of the spring Thus, the expendable unit equipped with its springs makes it possible to maintain in a rest position (between two flashes) the communication between the cavity and the aeration orifice or orifices of the housing. Passages are for example arranged in the box, on either side of the window, in order to ensure the communication of air towards the cavity.

BRIEF DESCRIPTION OF THE DRAWINGS

Other characteristics and advantages of the invention will become apparent during the following description of several embodiments, given by way of non-limitative examples, with reference to the attached drawings, in which:

FIGS. 1A and 1B each show a front and profile view respectively, of the head of a hair-removal device according to the invention;

FIG. 2 is a perspective view of an expendable unit including the flashlamp in an embodiment of the invention;

FIG. 3 shows a perspective view of a hair-removal device according to the invention for the rest position;

DETAILED DESCRIPTION OF THE DISCLOSURE

Figure 4A:
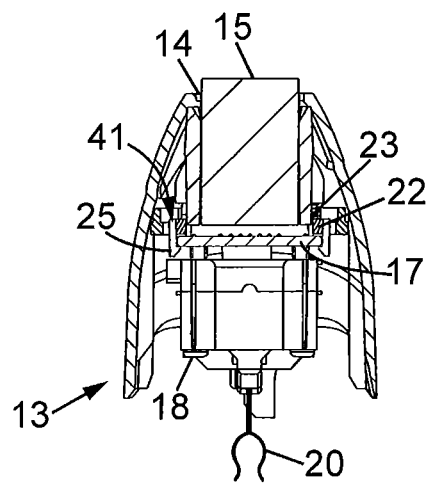
FIG. 4A is a view along the plane A-A in FIG. 1A of the head of the hair-removal device for the rest position of the device.

The same references in different figures denote identical or similar elements. In what follows, by flashlamp 10 is meant any incoherent electromagnetic energy source suitable for a hair removal treatment. More generally, the phraseology and the different terminologies used only serve the purposes of description and should not be interpreted limitatively.

According to the present invention, it is possible to carry out hair removal by exposing a hairy area to intense electromagnetic energy in the form of flashes of light. This energy heats the hairs and in particular affects the follicles without damaging healthy skin. An optically transparent gel of a type known per se is preferably applied before the treatment. The gel serves to eliminate the air gap comprised between the end of the coupler and the surface of the epidermis. The gel therefore contributes to the efficiency of the optical transmission.

The hair-removal device 11 comprises a flashlamp 10, for example and in no way limitatively a xenon flashlamp, making it possible to cover a relatively extensive area, for example between 4 and 50 cm$^2$. This makes it possible to reduce the treatment time. The shape of the beam can be a regular rectangular shape or a similar symmetrical shape with a surface area comprised between 6 and 44 cm$^2$.

Now with reference to FIGS. 1A, 1B, 2 and 3, the flashlamp 10 is accommodated inside a housing that can be split into two housing portions (12, 13) one of which forms a handle 12 and the other a head 13. These two housing portions (12, 13) can assembled by locking via at least two peripheral tabs 13a on the head 13 each cooperating with an analogous groove g (FIG. 7), channel or cavity of the handle 12 which allows a freedom of movement along a longitudinal axis passing through the handle 12 and the head 13. Naturally, other appropriate assembly methods can be used.

By way of example as illustrated in FIG. 3, the head 13 has an end opening 14 through which a coupler 15 passes that makes it possible to direct the electromagnetic energy originating from the flashlamp 10 onto a skin surface during a hair removal treatment carried out by the device 11. In other words, the coupler 15 defines an optical conduit between the flashlamp 10 and the skin surface to be treated, preferably coated with a gel. The coupler 15 can be at least quartz-based or made of another transparent solid material. The coupler 15 can be constituted by one or more parts; it can be a simple glass pane.

A power source (not shown) can be placed inside the handle 12 and connected to the flashlamp 10. The power source can be autonomous and recharged via a connector provided in the handle 12 for connection to a hair-removal device management base 11 or to the mains. The housing illustrated in the figures can be grasped and carried in one hand. The hair-removal device 11 formed by the housing and its contents can thus deliver a plurality of flashes in independent and autonomous manner.

With reference to FIG. 3, the optical coupler 15 placed in the head 13 projects beyond the end opening 14 of the head 13. The internal volume of the housing portion forming the head 13 makes it possible to accommodate the main part of the coupler 15. Furthermore, the flared shape of the head 13 in the embodiment shown makes it possible to cause the air to circulate laterally from the flashlamp 10 arranged to the rear of the coupler 15, as well as in a space or cavity C (FIG. 4B) defined between the flashlamp 10 and the coupler 15.

In the embodiment shown, the handle 12 can be actuated as a whole by the user in a pushing movement in straight translation towards the free end of the head 13 held against a surface to be treated in order to trigger a flash. During operation, the surface to be treated blocks the head 13, which makes it possible to displace the handle 12 by a pushing movement. This translation movement being relative, it can equally be considered that the handle 12 is kept fixed and that the head 13 is pushed into the handle 12, or also that these two housing portions are both displaced towards each other. The extent of the displacement can substantially correspond to the distance d between the edge 16 of the circumference of the head 13 and an adjacent external edge B of the handle 12. The edge 16 to the rear of the head 13 defines an opening which is large enough to allow the insertion of the front end of the handle 12 into the internal volume of the head 13.

The displacement of the handle 12 is permitted by the space left between the flashlamp 10 and the coupler 15, inside the head 13. An elastic return system maintains by default the internal gap between the housing portion forming the handle 12 and the housing portion forming the head 13, so that air can easily circulate in this space between two flashes.

The drive connection associated with the handle 12 will now be described with reference to FIGS. 2, 4A, 4B, 5A, 5B and 6.

In a manner known per se, the flashlamp 10 corresponds to an electromagnetic source accommodated in a box 18, the assembly being able to form an expendable unit (10, 18) which can be removed from the housing. As shown in FIG. 2, the box 18 has an end surface with a window 19 to allow the rays from the flashlamp 10 to escape. The box 18 also comprises on the one hand first fixing elements 20 arranged opposite the window, and on the other hand second fixing elements 21 arranged on the periphery of the window 19. The first fixing elements 20 ensure the mechanical connection between the expendable unit (10, 18) and the handle 12, whilst the second fixing elements 21 help to wedge the expendable unit (10, 18) in a determined position in relation to the head 13 of the hair-removal device 11. The fixing made possible by these respective elements (20, 21) is of detachable type and the expendable unit (10, 18) can be removed manually, without using a tool.

The mechanical connection between the expendable unit (10, 18) and the handle 12 makes it possible to push the flashlamp 10 towards the coupler 15 when the user actuates the handle 12. Naturally, the actuation making it possible to displace the flashlamp 10 can also be initiated differently, depending on the structure of the mobile component or the drive mechanism chosen in order to allow this displacement.

Figure 6:
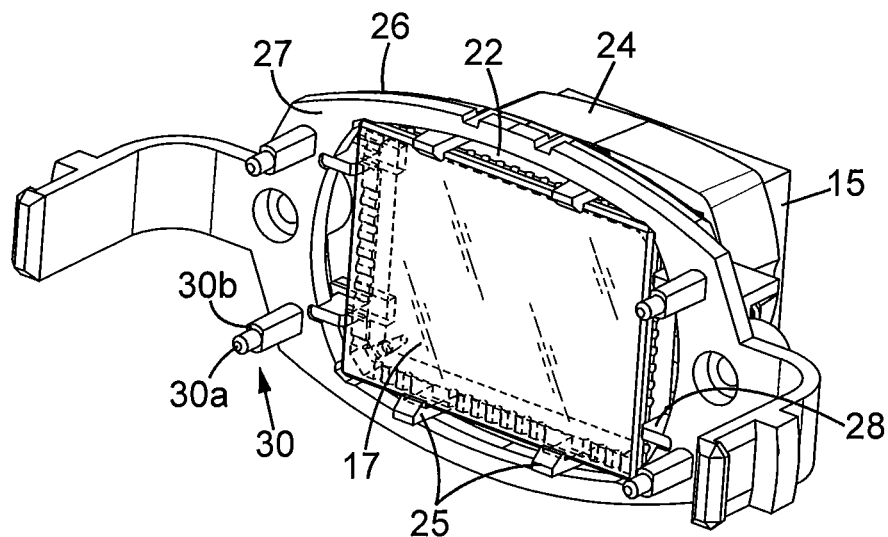
FIG. 6 is a perspective view illustrating the position of the filter in the head of the hair-removal device for the actuated position of the device.

As indicated in FIG. 6, at least one filter 17 is provided in the housing to filter the beam originating from the flashlamp 10. This filter 17 can be arranged between the flashlamp 10 and the coupler 15. This filter 17, or in an alternative embodiment several filters, are used in order to control the spectrum generated by the flashlamp 10. An absorption filter 17 can thus be used. Under certain conditions of use, the filter 17 could also be removed.

Figure 4B:
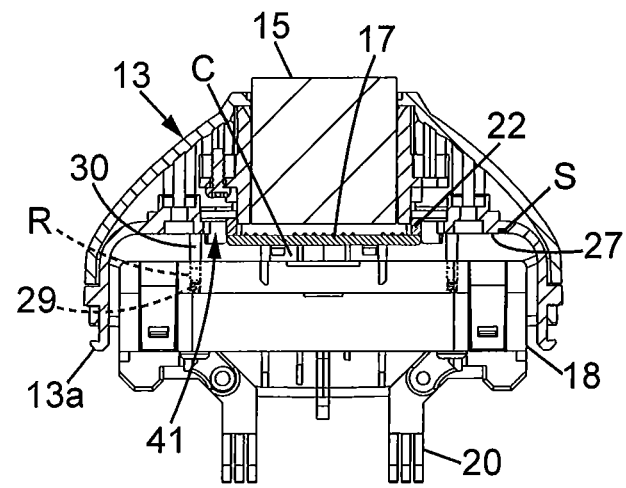
FIG. 4B is a view along the plane B-B in FIG. 1B of the head of the hair-removal device for the rest position of the device.
Figure 5A:
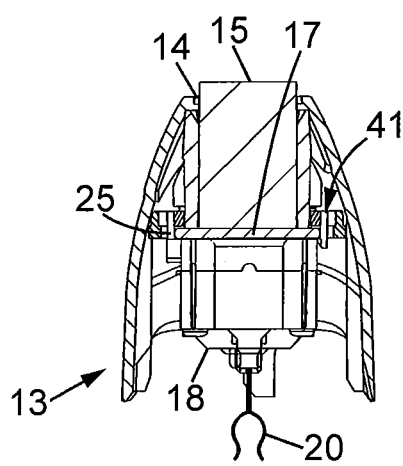
FIG. 5A shows a view along the plane A-A in FIG. 1A of the head of the hair-removal device for the active position of the device.
Figure 5B:
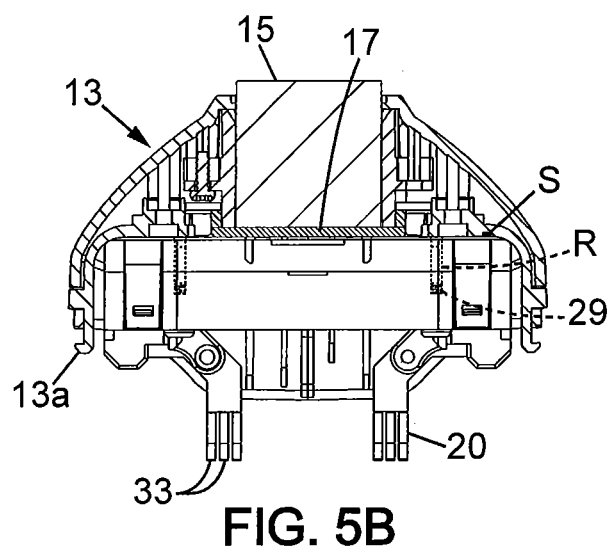
FIG. 5B shows a view along the plane B-B in FIG. 1B of the head of the hair-removal device for the active position of the device.

With reference to FIGS. 4A, 4B, 5A and 5B, the hair-removal device 11 according to the invention has a deactivated position or rest position (FIGS. 4A and 4B) and an activated position (FIGS. 5A and 5B). In the rest position, the ventilation or aeration circuit ventilates the filter 17 via the cavity or cavities C adjacent to the filter 17. The cavity C communicates with the outside in this position, for example via side passages P. In the activated position, the box 18 accommodating the flashlamp 10 is displaced in order to move close to the flashlamp 10 of the filter 17. After this relative moving together of the box 18 and the head 13, the cavity C adjacent to the flashlamp 10 is isolated from the rest of the housing and forms a narrow enclosure that limits the light escaping laterally and can thus promote the optical transmission towards the opening 14. On the side opposite this opening 14, the flashlamp 10 is surrounded by a reflector arranged in the box 18. The cavity defined by the reflector is extended by the cavity C. It will be understood that leaving the active position leads to an intake of air in front of the window 19, the air arriving via passages passing through the box 18 and/or lateral passages. The air can pass through the box 18 in spaces arranged essentially level with the external electrodes of the flashlamp 10 (passages on the outside of the reflector as can be seen in FIG. 2 for example). Ventilation of the cavity C is thus achieved. It will be understood that the arrangement made in the box 18 can serve to channel air originating for example from a fan incorporated into the device 11 and destined for the cavity C, and advantageously also makes it possible to cool down the electrodes.

In the embodiment shown, the filter 17 is substantially flat and arranged in the housing in its intermediate position using a fixing arrangement 41 integral with the head 13. As shown in particular in FIG. 6, this fixing arrangement 41 comprises a tubular-shaped support 22, for example in the form of a frame, with dimensions comparable to those of the filter 17. This support 22 has a degree of freedom in translation between the coupler 15 and the flashlamp 10 installed in the housing, along an axis perpendicular to a plane defined by the filter 17.

As shown in FIG. 4A which corresponds to a retracted position of the expendable unit (10, 18) accommodating the flashlamp 10, one or more elastic stress components 23 such as springs are placed longitudinally, for example in a peripheral arrangement around the coupler 15, in order to hold the support 22 and the filter 17 at a distance from the coupler 15. These elastic stress components 23 are for example supported on a frame or an internal ring 24 formed around the coupler 15, at the end of the head 13.

For the activated position of the hair-removal device 11 shown in FIGS. 5A and 5B, these elastic stress components 23 can be compressed by at least one support surface of the support 22 of the filter 17. In this activated position, the expendable unit (10, 18) and the filter 17 are both moved close to the coupler 15. Contact is for example established between the filter 17 and the coupler 15 in this position. The thrust contact between the support 22 of the filter 17 and the box 18 is carried out at a distance from the filter 17, by means of clipping tabs 25 retaining between them the filter 17 and extending towards the rear of the head 13. There are at least three clipping tabs 25, and in particular four in the embodiment shown in FIG. 6 (activated position).

In its extended position (activated position of the device), as illustrated in FIG. 5A, the box 18 is supported on the free end of the clipping tabs 25 and thus pushes the support 22 of the filter 17 as a whole in towards the front of the head 13. The pushed-in position of the support 12 of the filter 17 is shown in FIG. 6. The end of travel for this pushing-in of the support 22 can be prescribed by the joint between the edge 16 of the head 13 and the edge B of the handle. Thus, the filter 17 held on its support 22 can be precisely positioned against the coupler without being deformed, which contributes to the maintenance of the integrity of the filter 17. In the embodiment shown in FIG. 3, the edges (13, B) have a complementary shape. In the example illustrated in FIGS. 5A and 5B, this pushed-in position corresponds to a bringing of the filter 17 into contact against the coupler 15.

With reference to FIG. 6, the housing portion forming the head 13 can comprise a tubular portion 26 that surrounds the support 22 and makes it possible to guide the latter. The tubular portion 26 has for example an internal surface with slots. Projecting elements 28 or radial projections from the support 22 can slide in these guide slots.

The tubular portion 26 also defines a surface 27 oriented towards the rear of the head 13 and making it possible to guide a flow of air parallel to the filter 17, as illustrated in FIG. 4B in the deactivated position of the device 11. The fact that the filter 17 can be displaced makes it possible to define in the housing, for the deactivated position, spaces on either side of the filter 17 in order to allow a cooling of the latter. The translation movement or other appropriate movement makes it possible to increase the spacing between the filter and the flashlamp during the return to the deactivated position, such that the air entering the intermediate volume thus created can cool down the surface of the filter 17 efficiently by convection. Being able to ventilate the filter 17 on both its surfaces allows efficient cooling when the energy supplied is high. Furthermore, the filter 17 is thus prevented as far as possible from transmitting its thermal energy to the optical conduit defined by the coupler 15. Cooling on only one surface can also be satisfactory for applications with a lower level of energy. The separation or distancing of the filter 17 in relation to the elements that accumulate heat (xenon tube and reflector) advantageously cuts down the possibilities of heat transmission, in particular to the coupler 15. The fineness of the filter 17 also makes it easier to cool down.

The housing can incorporate one or more reduced format fans (not shown), for example at the handle 2. With reference to FIGS. 4A and 4B, the cavity or space between the front surface of the box 18 and the filter 17 can be ventilated inside the housing via passages passing through and/or around the box 18. In the same way, the space formed between the filter 17 and the coupler 15 can be ventilated. The opening of the passages through the box 18 can for example be shifted laterally outwards in relation to the ends of the filter 17. The air leaving these passages can then, in the rest position, circulate fully in the cavity or cavities C adjacent to the filter 17. It will thus be understood that the filter 17 is efficiently cooled between two flashes. It will be understood that the mobility to the activated position of the device 11 makes it possible to limit the losses of light (improvement in energy output). The mobility towards the rest position of the device 11 makes it possible to reduce the state of confinement around the flashlamp 10, which limits the possibilities for efficient aeration of the latter.

As can be seen in FIGS. 4B, 5B and 6, the housing also has one or more elongated components 30 that extend from the guiding surface 27 inside the housing up to a free end 30a in the form of a stud, in a general direction perpendicular to the filter 17 and in a direction opposite the direction of radiation. These elongated components 30 penetrate with their free end 30a into recesses R in the box 18. These cylindrically shaped recesses R form the second fixing elements 21 of the box 18. The box 18 is thus made integral in rotation with the housing portion forming the head 13. The elongated components 30 on the other hand leave a freedom of movement in translation along a longitudinal axis of the hair-removal device 11. The box 18 is thus guided in translation by these elongated components 30 which can be presented in the form of rods.

With reference to FIG. 6, the elongated component 30 has a shoulder 30b and ends in a rod portion up to the free end 30a. The box 18 has at least one recess R with a base and a spring 29 provided in the recess R, the recess R making it possible to receive at least part of said elongated component 30, the spring 29 having a first end supported on the base and a second end supported on the shoulder 30b, said spring 29 being compressed for the second position in which the flashlamp 10 and the filter 17 are moved close together.

In the embodiment shown in FIG. 5B corresponding to the activated position of the hair-removal device 11, each of the elongated components 30 completely penetrates into the corresponding recess in the box 18. The latter is then supported by its front end surface on the guiding surface 27. It will be understood that in the activated position, the cavity or space for the aeration of the filter 17 is eliminated or reduced and crossed through by aeration passages. In order to prevent a user from triggering several flashes in this position, a sensor S is for example provided in the housing that delivers a piece of information representative of the occupation of the activated position with a moving together of the flashlamp 10 and the filter 17. A control device associated with the generator which supplies the flashlamp 10 is also provided in the housing to receive one or more pieces of information from this sensor S and allow the emission of a single flash of light when the activated position has been detected by the sensor S.

In practice, after having chosen the area to be treated, the user must exert pressure on the handle 12 in order to obtain the activated position, a flash then being triggered. Then, the user releases the pressure and allows the handle 12 to return to its default deactivation position. During the pressure release time, the device 11 can be displaced in order to be applied to the next area to be treated.

Figure 7:
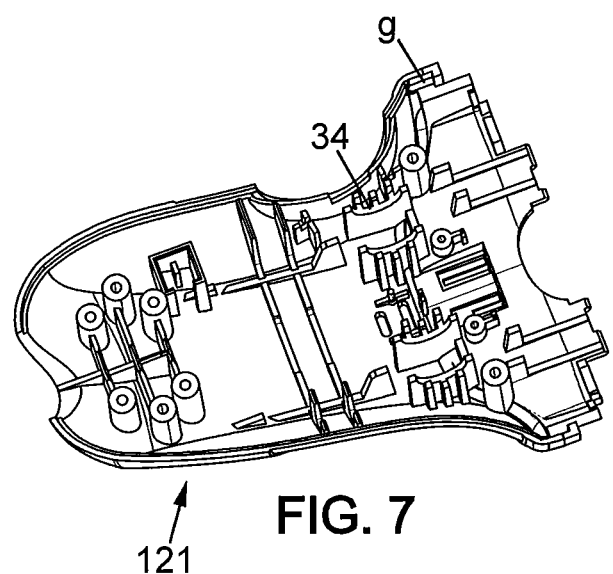
FIG. 7 shows an upper shell of the handle of a hair-removal device according to the invention.
Figure 8:
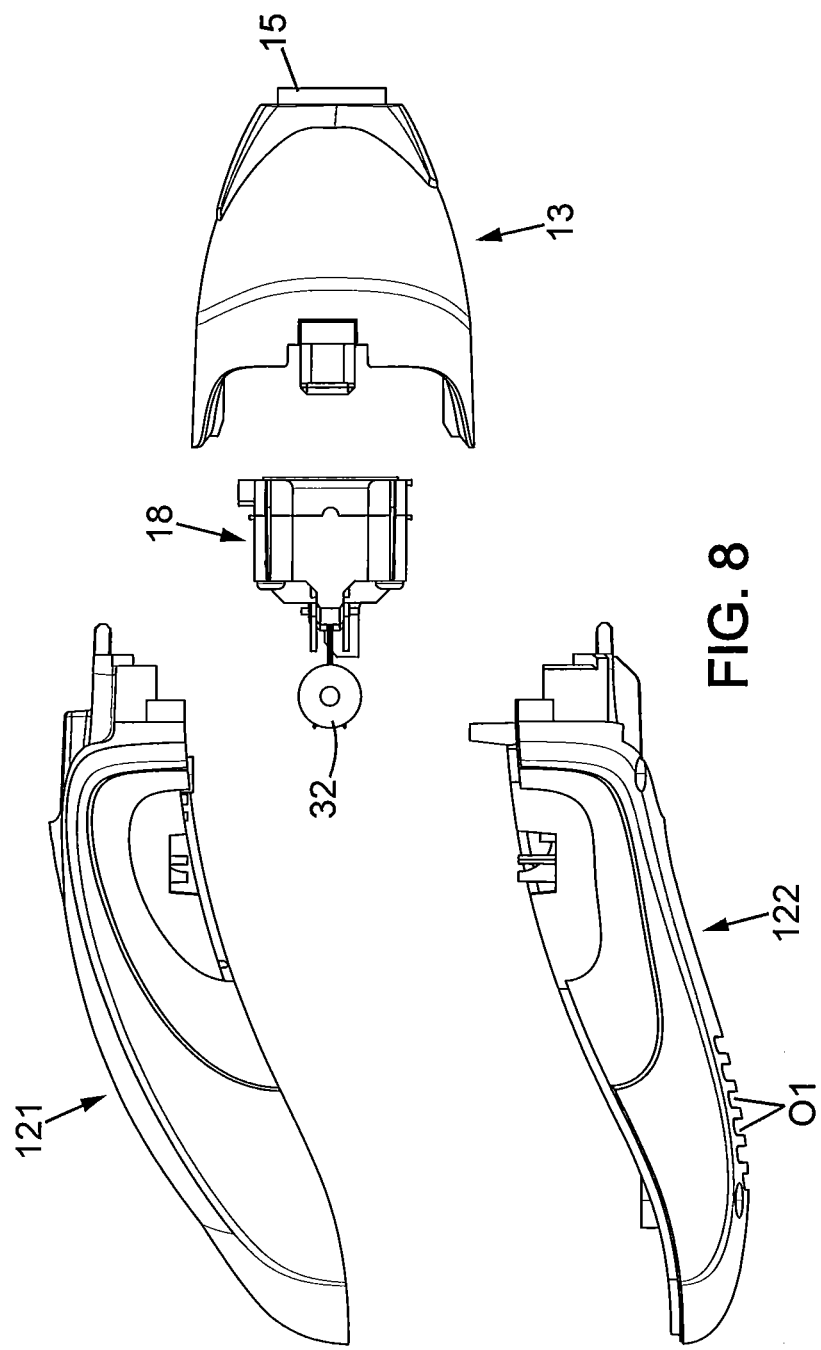
FIG. 8 shows an exploded view of a hair-removal device according to the invention.

With reference now to FIGS. 3, 7 and 8, the housing portion forming the handle 12 can have external air intake orifices 01, whilst internal air delivery orifices 02 can be provided at the joint between the handle 12 and the head 13. Two complementary shells (121, 122) can be assembled in order to form the handle 12, as illustrated in FIG. 8. The lower shell 122 has for example several orifices 01 distributed along the handle 12. The power supply generator of the flashlamp 10 can be accommodated at the rear of the housing. Cylinders 32 made of copper, held by concave supports 34 formed integrally with the shells (121, 122) of the handle 12, are in direct electric contact with an internal end part of the electric connectors of the box 18. The significant mass of these cylinders 32 leads to significant thermal inertia making it possible to reduce the heating at the electric contacts. In one embodiment, the size of the external electrodes of the tube of the flashlamp 10 is significant to limit the thermal heating. These external electrodes extend for example over more than a centimetre. In order to increase their thermal inertia, they can have a large diameter and a relatively great length.

The box 18 can be equipped with copper-beryllium alloy $CuBe_2$ based spring contact strips 33. These contact strips 33 also form at least part of the first fixing elements 20 provided for fixing the box 18 to the housing portion forming the handle 12. These contact strips 33 extend the opposite way to the coupler 15 and are spaced in relation to each other and arranged in the form of an open clipping collar, as illustrated in FIGS. 4A to 5B. The contact strips 33 can thus be fixed to components, such as cylinders, which are elongated transversally along an axis perpendicular to the elongated components 30 guiding the translation movement of the box 18 accommodating the flashlamp 10. In the box 18, the connection with the external electrodes of the flashlamp 10 can be in a form completely similar to those of the contact strips 33.

The beryllium material $CuBe_2$ has characteristics that are optimized for the electric conduction, heat conduction and elasticity necessary for "clipping"/"unclipping" during the changing of the expendable unit (10, 18). Certain parts made of $CuBe_2$ and copper can be gilded with fine gold in order facilitate the 300 V/300 A electric contacts. This electric connection part is for example ventilated by one or more fans placed in the handle 12.

The assembly of the expendable unit (10, 18) in the housing can be carried out in simple manner by the user, for example during the replacement of the flashlamp 10. The housing can first be separated into two by removal of the head 13. The box 18 is then coupled to the handle 12 by the first fixing elements 20 (via the cylinders 32). This involves a clipping operation. It then remains to close the housing by clipping the head 13 onto the handle 12 by the two tabs 13a. The device is then assembled and operational.

One of the advantages of the device is better energy management which makes it possible to equal the characteristics of the best professional material in a totally optimized bulk.

It must be obvious to persons skilled in the art that the present invention allows embodiments in numerous other specific forms without departing from the field of application of the invention as claimed. In particular, although the description relates to an appliance of which a part of the housing forming the handle 12 can actuate the drive system by pushing, it will be understood that any other mode of actuation can be used (rotation, helical movement, pulling, actuation of a pushbutton or trigger, etc.) in order to lead to an analogous result. Thus, a support structure of the filter 17 and/or of the coupler 15 can be made mobile relative to the rest of the housing which comprises the flashlamp 10. The support on the skin surface to be treated makes it possible for example to actuate the displacement of this mobile structure in this case.

Moreover, the decoupling between two flashes can simply consist of the separation of the filter 17 from the flashlamp 10 (single decoupling) instead of separation of the filter 17 from both the flashlamp 10 and the coupler 15 (double decoupling). Ventilation of the entire surface of the filter 17 remains effectively ensured with a single decoupling. Alternatively or complementarily, the closing of the cavity C can also be triggered by use of one or more mobile components displacing walls blocking communication passages with the cavity C or any similar space adjacent to the flashlamp 10.

The invention claimed is:
1. A radiation pulses emitting device comprising:
   a phototherapy flashlamp,
   a housing, said flashlamp being arranged inside the housing, the housing having an opening through which electromagnetic energy originating from the flashlamp can be transmitted towards a skin surface,
   wherein the housing comprises:
   a first housing portion that comprises said opening;
   a second housing portion allowing a displacement in translation between the first housing portion and the second housing portion, the flashlamp being integral with the second housing portion;
   a cavity adjacent to the flashlamp, the cavity being defined inside the first housing portion;

at least one aeration orifice;
a communication passageway between the cavity and said aeration orifice, said cavity and said aeration orifice each extending at a distance from the opening of the housing; and
at least one mobile component, which can be moved between a first position, in which said cavity communicates with said aeration orifice and a second position, for which said cavity is closed in order to limit the light escaping from said opening of the housing; and
wherein the flashlamp extends inside the first housing portion when the cavity is closed.

2. The device according to claim 1, wherein said mobile component interferes with said communication passageway when said mobile component is moved from the first position to the second position.

3. The device according to claim 1, wherein
the mobile component is formed by one of said first and second housing portions.

4. The device according to claim 3, in which the first housing portion is a head and the second housing portion forms a handle which can be grasped by a hand, said mobile component making it possible to move the flashlamp towards the free end of the head when the head is supported on a surface outside the device.

5. The device according to claim 1, comprising inside the housing:
a coupler making it possible to direct the electromagnetic energy originating from the flashlamp onto a skin surface; and
a filter inserted between the flashlamp and the coupler;
wherein the flashlamp is arranged opposite and at a distance from the filter for said first position.

6. The device according to claim 1, wherein the flashlamp is part of an expendable unit that can be removed from the housing.

7. The device according to claim 6, wherein the expendable unit comprises a box for accommodating the flashlamp, said box comprising:
an end surface having a window to allow electromagnetic energy from the flashlamp to escape, the window having a periphery;
first fixing elements defining ends opposite said end surface;
second fixing elements arranged on the periphery of the window;
the first fixing elements being configured to engage with at least one piece elongated in a first direction, whilst the second fixing elements are configured to engage with at least one elongated component that is elongated in a second direction perpendicular to the first direction;
and wherein the inside of the housing has a surface for guiding a flow of air parallel to the filter and from which said elongated component extends in a general direction perpendicular to the filter.

8. The device according to claim 7, wherein said elongated component has a shoulder and ends in an end rod portion, the box comprising at least one recess with a base and a spring provided in the recess, the recess making it possible to receive at least part of said elongated component, the spring having a first end supported on the base and a second end supported on the shoulder of the elongated component, said spring being compressed for said closed position in which the flashlamp and the filter are moved close together.

9. The device according to claim 7, wherein the first fixing elements comprise metal power conducting elements.

10. The device according to claim 1, comprising:
a sensor capable of delivering a piece of information representative of the occupation by said mobile component of said closed position.

11. In the device according to claim 1, an expendable unit comprising:
a phototherapy flashlamp;
a box for accommodating the flashlamp, having an end surface with a window to allow electromagnetic energy from the flashlamp to escape, the window having a periphery;
on a side of the end surface and on the periphery of the window, at least one recess in which a spring is placed, which has an end mobile between a compressed retracted position allowing the cavity of the device to be closed in order to limit electromagnetic energy escaping except towards the opening and an extended position for which the cavity communicates with the aeration orifice of the device; and
at least one element for fixing the box to the housing.

12. The device according to claim 1, wherein the housing comprises a handle which extends at a distance from the opening of the housing, and wherein said at least one aeration orifice comprises an external air intake orifice provided in the handle.

13. A radiation pulses emitting device, comprising:
a phototherapy flashlamp;
a housing, said flashlamp being arranged inside the housing, the housing having an opening through which electromagnetic energy originating from the flashlamp can be transmitted toward a skin surface;
wherein the housing comprises:
a cavity adjacent to the flashlamp;
at least one aeration orifice;
a communication pathway between the cavity and said aeration orifice, said cavity and said aeration orifice each extending at a distance from the opening of the housing; and
at least one mobile component, which can be moved between a first position, in which said cavity communicates with said aeration orifice and a second position, for which said cavity is closed in order to limit the light escaping from said opening of the housing,
wherein the flashlamp is part of an expendable unit that can be removed from the housing, and wherein the expendable unit comprises:
a box for accommodating the flashlamp, having an end surface with a window to allow electromagnetic energy from the flashlamp to escape, the window having a periphery;
on a side of the end surface and on the periphery of the window, at least one recess in which a spring is placed, which has an end mobile between a compressed retracted position allowing the cavity of the device to be closed in order to limit electromagnetic energy escaping except towards the opening and an extended position for which the cavity communicates with said at least one aeration orifice; and
at least one element for fixing the box to the housing.

* * * * *